United States Patent [19]
Smith

[11] Patent Number: 5,748,699
[45] Date of Patent: May 5, 1998

[54] APPARATUS FOR APPLYING X-RAYS TO AN INTERIOR SURFACE OF A BODY CAVITY

[76] Inventor: Donald O. Smith, 16 Dewey Rd., Lexington, Mass. 02173

[21] Appl. No.: 725,732

[22] Filed: Oct. 4, 1996

Related U.S. Application Data

[60] Provisional application No. 60/004,921 Oct. 6, 1995.
[51] Int. Cl.[6] .................................................. A61N 5/10
[52] U.S. Cl. .......................... 378/65; 378/64; 604/20
[58] Field of Search ............................. 604/20, 21, 104, 604/96, 99; 378/65, 64, 204

[56] References Cited

U.S. PATENT DOCUMENTS 5,621,780  4/1997  Smith et al. ............................. 378/65

*Primary Examiner*—Don Wong
*Attorney, Agent, or Firm*—Lappin & Kusmer LLP

[57] ABSTRACT

The present invention is directed to an assembly for stretching a body cavity to a predetermined shape. The assembly includes an inelastic balloon that is affixed to the distal end of a balloon-tube. The tube defines an interior channel extending along a central axis that is contiguous with the interior of the balloon such that inflation and deflation of the balloon is controllable from the proximal end of the tube. When inflated the balloon defines a predetermined surface contour disposed about an interior region extending along a balloon axis. An alignment device operative from the proximal end of the tube provides for selectively aligning the central and balloon axes to a predetermined angular orientation. The catheter may be part of a kit for providing radiation treatment to a body cavity, including an x-ray source including an x-ray generator disposed at or near a target end of an elongated tubular element wherein the tubular element is slidably positionable within the interior channel such that the target end is positionable within the balloon when inflated. Inflating the balloon within a body cavity and positioning the target end inside the inflated balloon allows delivery of a specifically contoured dose of radiation to the tissue lining the body cavity.

43 Claims, 10 Drawing Sheets

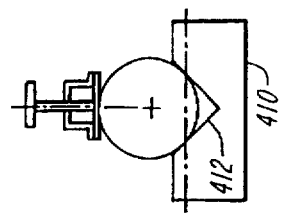
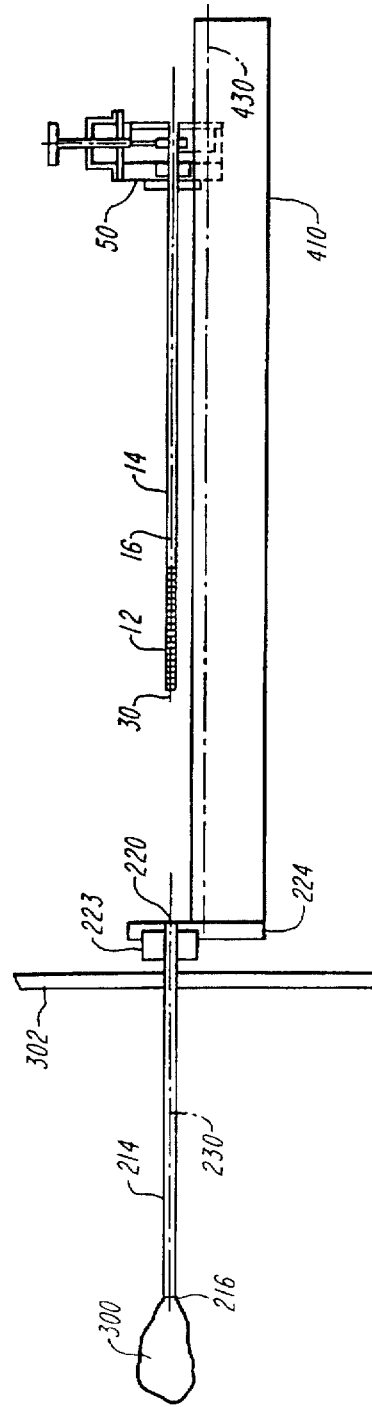

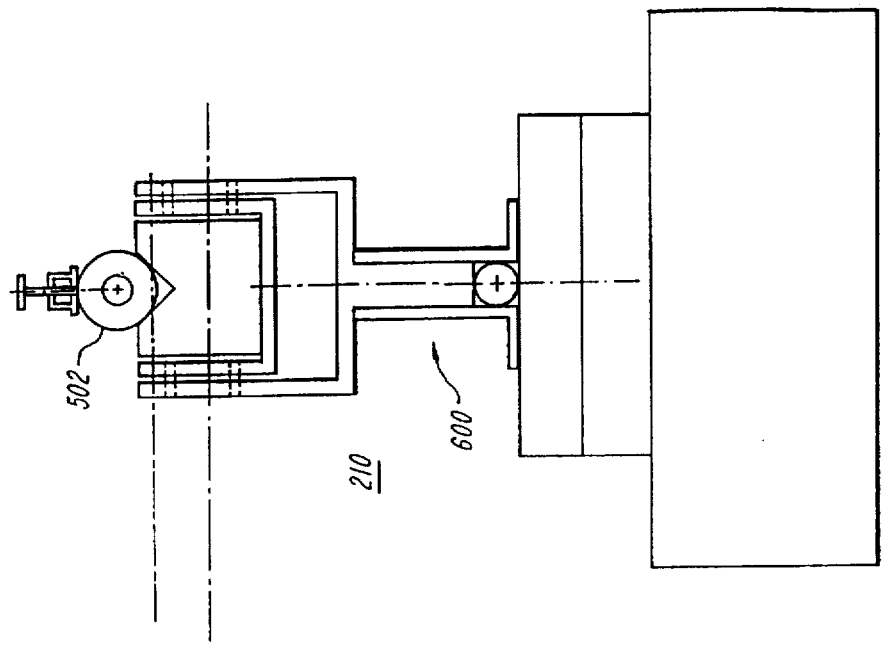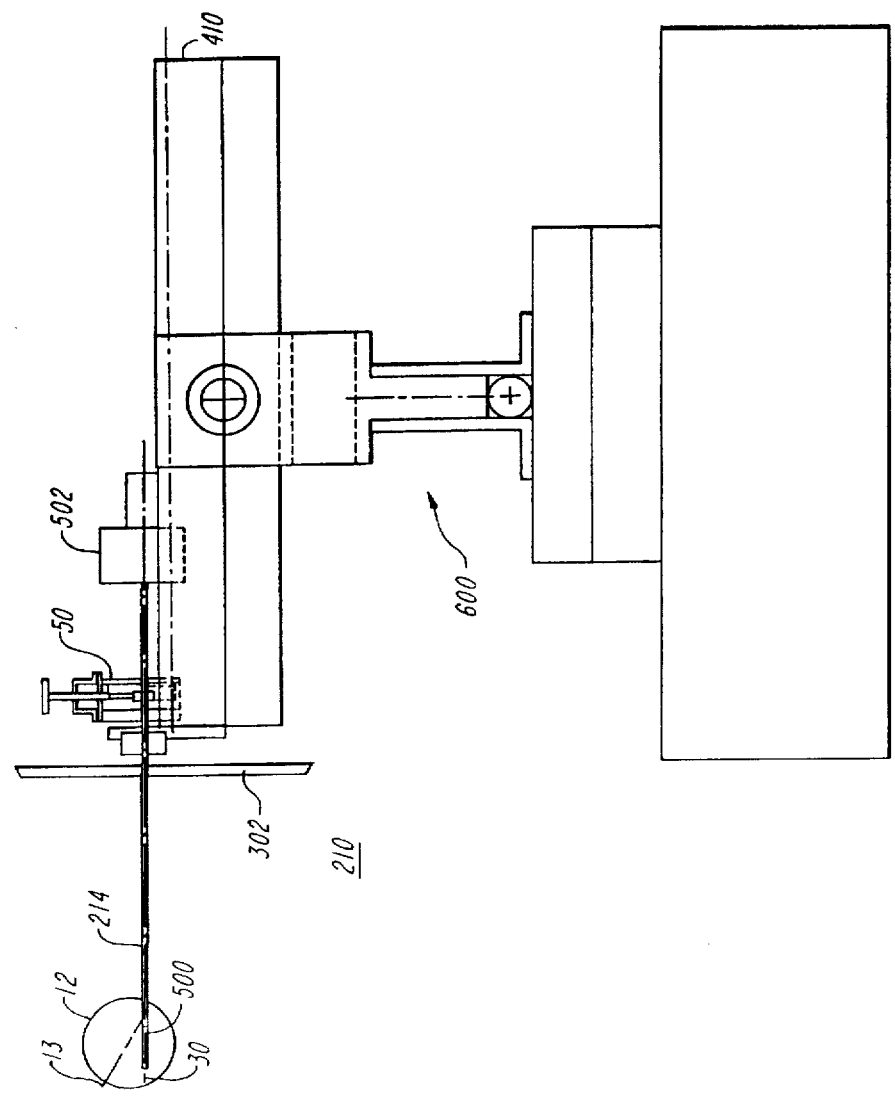

APPARATUS FOR APPLYING X-RAYS TO AN INTERIOR SURFACE OF A BODY CAVITY

REFERENCE TO RELATED APPLICATION

This application claims the benefit of U.S. patent application Ser. No. 60/004,921, entitled Improved Apparatus for Applying X-rays to an Interior Surface of a Body Cavity, filed Oct. 6, 1995.

BACKGROUND OF DISCLOSURE

The present invention relates to a miniaturized, low power, programmable x-ray source for use in delivering specifically contoured doses of x-rays to a specified region. More specifically, the invention relates to apparatus and methods for delivering desired x-ray flux to interior surfaces of body cavities.

X-radiation applied to the soft tissue lining body cavities is known to be useful in the treatment of certain cancers, including cancer of the bladder, vagina and cervix, urethra, uterus, colon and rectum. In an ideal treatment for many conditions, only the surface of the body cavity, i.e., the target tissue, is exposed to the radiation. However, most conventional, radiation therapy utilizes an external radiation source which directs relatively high energy, and thus tissue-damaging, x-rays toward the patient, so that the x-rays must first penetrate the skin and other tissue of the patient, prior to reaching the tissue lining the body cavity. Undesirable radiation of non-target tissue is thus an unavoidable consequence of having a conventional x-ray source located outside the patient's body. Further, the use of relatively high energy, and thus tissue damaging, x-rays are required to insure that a sufficient dose is delivered to the target tissue.

Conventional methods of radiation treatment for tissue lining body cavities also fail to provide the ability to deliver a specific dose of radiation to the target tissue, which may have an arbitrary contour. In some cases, it is desirable to provide a substantially uniform dose of radiation over a relatively large target area. In other cases, specifically contoured non-uniform doses may be desired. As used herein, the term "isodose contour" refers to a surface over which the x-ray flux density is substantially constant. In the context of an interior surface, or lining of a body cavity, a uniform dose implies generating an x-ray distribution having an isodose contour that is coincident with the interior surface of the cavity.

Some of these disadvantages of the prior art approaches can be overcome through the use of a miniaturized low power x-ray source, such as the one described in the above-referenced U.S. Pat. No. 5,153,900 granted to Nomikos et al. That x-ray source includes an elongated tube extending along a source axis, and has an electron beam generator at one end which generates and directs an election beam along the source axis to the other end and in here it is incident upon a target which is reprone to the beam to generate x-radiation.

That source can be inserted into a patient's body, and immediately adjacent to a tissue to be treated, and then activated to generate x-rays from within, permitting generation of x-rays from points local to the target tissue. When such an x-ray source is used to treat the tissue lining a body cavity, the x-rays need not pass through the patient's bone mass, and skin, and other tissue prior to reaching the target tissue.

One useful apparatus for delivering radiation to the interior surface of a body cavity uses a combination of a miniaturized low power x-ray source of the type disclosed in U.S. Pat. No. 5,530,900, and an inflatable balloon. The above-referenced U.S. patent application Ser. No. 08/273,645, entitled X-ray Apparatus for Applying a Predetermined Flux to an Interior Surface of a Body Cavity, describes one such combination. This apparatus uses a guidance (or balloon) tube with a balloon affixed to its distal tip, where the balloon stretches the body cavity to a desired known shape, such as a sphere. The x-ray source is advanced through the balloon-tube so that its x-ray generating distal tip is positioned at a predetermined location, for example, the center, within the inflated balloon, and then is activated. In cases where it is desired to apply a uniform dose to the lining of a body cavity having a flexible defining boundary (such as the bladder), a substantially spherical (when inflated) balloon is positioned in the cavity and inflated, thereby forcing a spherical shape to the defining boundary, and thus the lining. Then a substantially omni-directional x-ray source is positioned at the center of the inflated balloon. With such a configuration, x-rays generated from within the inflated balloon establish a substantially uniform dose at the surface of the body cavity.

One important aspect of that approach is the ability to locate the x-ray source at a predetermined location within the body cavity. Inflating the balloon can stretch the body cavity to a known shape, but internal pressures near the cavity can cause the balloon-cavity structure to shift in position relative to the balloon tubes, thereby causing a misaligmnment between the balloon axis and the axis of the x-ray source. If the x-ray source can not be positioned accurately, it then becomes difficult to deliver a uniform dose to the surface of the body cavity.

Another combination of an x-ray probe and a balloon is described in U.S. patent application Ser. No. 08/273,963, entitled Improved X-ray Apparatus for Applying a Predetermined Flux to an Interior Surface of a Body Cavity. In this combination, opposite ends of a balloon are permanently affixed to and disposed about an extension of a balloon-tube, which passes along a diameter of the balloon when inflated. In operation with this configuration, the balloon-tube and deflated balloon are inserted into the body such that the deflated balloon is initially positioned within the cavity and the balloon is then inflated. The balloon-tube and its extension maintain alignment between the balloon-tube and the balloon. The x-ray probe is then inserted into the balloon-tube and positioned with its x-ray generating distal tip at a predetermined location along a diameter of the balloon so that x-rays can be generated from a known location within the body cavity.

One problem the with latter configuration is that the deflated balloon, when packed around the balloon-tube, forms a structure that is relatively large in diameter making insertion into and retraction from body passageways difficult. This is an important factor for relatively small passageways, such as the urethra, into which the structure is inserted for x-ray treatment of the bladder. Further, in such configurations, the balloon-tube is typically only partially transmissive of x-rays and interferes with the ability to deliver a specifically contoured dose to the target tissue.

Also, with the above described configurations, the radiating tip of the probe can not be placed close to a cavity wall in a manner permitting radiation of local lesion on that wall.

It is therefore an object of the invention to provide an improved method and apparatus for delivering a specifically contoured dose of radiation to the tissue lining body cavities.

It is a further object of the invention to provide an apparatus, that includes a miniature low power x-ray source and a balloon, for delivering uniform or other desired doses of radiation to the tissue that lines a body cavity.

Other objects and advantages of the present invention will become apparent upon consideration of the appended drawings and description thereof.

SUMMARY OF THE INVENTION

The foregoing and other objects are achieved by the invention which in one aspect comprises a balloon assembly for stretching a body cavity to a predetermined shape. The assembly includes a guidance cannula, a balloon-tube and a balloon. The cannula is relatively rigid and has proximal and distal ends and extends along a cannula axis. The balloon-tube has proximal and distal ends and defines an interior channel extending along a central axis. The balloon-tube has an outer contour adapted to slidingly fit within the cannula so that the cannula and central axes are substantially coaxial. An inflatable substantially inelastic balloon is affixed to the distal end of the balloon-tube. The interior channel of the balloon-tube is contiguous with and connected to the interior of the balloon so that inflation and deflation of the balloon may be controlled from the proximal end of the balloon-tube. When inflated, the balloon defines a predetermined surface contour disposed about an interior region extending along a balloon attachment axis, or balloon axis, which extends across a diameter of the balloon from the junction of the balloon-tube and the balloon. The balloon axis intersects the central axis of the balloon-tube near the distal end of the balloon-tube.

In operation, the cannula may be inserted through a body passageway, e.g., the urethra, so that the distal end of the cannula is positioned near a body cavity, e.g., the bladder, and so that the proximal end of the cannula remains external to the body. The balloon-tube and balloon, when deflated, may then be inserted through the cannula so that the balloon is positioned beyond the distal end of the cannula and within a body cavity. The balloon may then be inflated and thereby stretch the body cavity to a predetermined shape. When the balloon-tube is inserted into the cannula, the central and cannula axes are normally coaxial.

Although the balloon axis and the central axis of the balloon-tube intersect, they are generally not axially aligned immediately following inflation of the balloon. While the balloon is substantially inelastic, the material forming the balloon at the attachment between the balloon and the balloon-tube somewhat flexible, permitting the orientation between the balloon axis and the balloon-tube to be easily changed. The angle between the central and balloon axes may be adjusted by rotating the cannula about the point of intersection of the balloon and central axes, thereby permitting adjustment of the central and cannula axes into a desired angular alignment. The assembly of an aspect of the invention farther includes an alignment mechanism that is operative from the proximal end of the cannula for selectively adjusting the angle between the balloon and cannula axes to a predetermined angular orientation. Preferably, the angle between the balloon and cannula axes is adjustable between zero and 90 degrees.

The alignment mechanism may include a reference mark, or region, which is detectable (e.g., optically detectable) from the interior of the balloon. The reference mark may be located at the intersection of the balloon and the balloon axis opposite the intersection of the balloon and central axes, and the reference mark may be located on the exterior of the balloon in the case of a transparent or translucent balloon, or on the interior of the balloon. The position of the reference mark relative to the cannula axis is determinable from within the interior region of the balloon, so that a user can observe the position of the mark relative to the cannula axis, and thus know the angular orientation of the balloon axis relative to the cannula axis.

In one form the reference mark may fluoresce in response to incident light in a predetermined spectral range. For that form, light in that spectral range may be directed via a filter to the balloon interior. An operator may manipulate the cannula axis relative to the balloon axis of the inflated balloon while monitoring the balloon interior via an output filter at a wave-length associated with the fluorescence, to detect fluorescent light from the reference mark and determine when the cannula axis is aligned with the balloon axis.

The assembly may also include an inflation assembly disposed near the proximal end of the balloon-tube for controlling the pressure in the interior region of the balloon. The inflation assembly may provide a gas flow path extending between a pressure source and the interior channel.

In another aspect, the invention provides a kit for applying x-rays to an interior surface of a body cavity. The kit includes an x-ray source that is cooperative with the above-described assemblies. The x-ray source includes an x-ray generator disposed at or near a target end of an elongated tubular element.

The x-ray generator may be an omnidirectional generator. The target end may also include a shield for controlling the spatial distribution of isodose contours of the x-rays emitted by the x-ray generator. The shield may be characterized by a selected x-ray transmission spatial profile.

The balloon when inflated may be spherical. However, the use of balloons having cylindrical, or other shape that may be desired for a particular cavity-to-be-illuminated. Symmetry, or no symmetry at all is also used for various forms of the invention. In such cases, to deliver a prescribed dose of radiation to the body cavity walls, the x-ray source may be masked, as is described for example in the above-referenced U.S. patent application Ser. No. 08/184,271, entitled X-ray Source With Shaped Radiation Pattern, and/or translated along the cannula axis during the exposure to radiation as described in U.S. Pat. No. 5,153,900.

BRIEF DESCRIPTION OF DRAWINGS

The foregoing and other objects of this invention, the various features the following description, when read together with the accompanying drawings in which:

FIGS. 5A and 5B are side and end views, respectively, of the kit, without the x-ray probe, shown in FIG. 4 further including a supporting V-guide;

FIGS. 8A and 8B are side and end views, respectively, of the kit shown in FIG. 7 further showing a support frame for supporting the V-guide and providing the spatial motions for aligning the cannula with the axis of the balloon-tube;

Like numbered elements in each FIGURE represent the same or similar elements.

DESCRIPTION OF THE PREFERRED EMBODIMENTS

Figure 1:
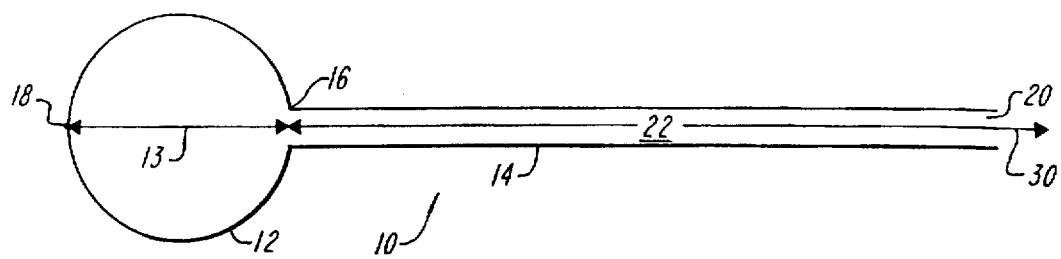
FIG. 1 is a cross sectional view of an apparatus according to the invention useful for providing radiation treatment to the interior surface of a body cavity, including a balloon-tube and an inflated balloon.
Figure 2:
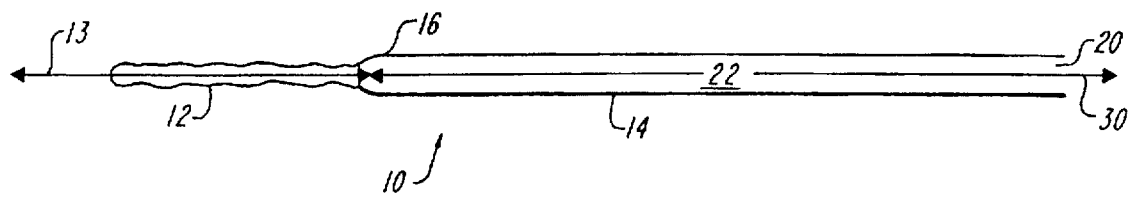
FIG. 2 is a view of the apparatus shown in FIG. 1 in which the balloon is deflated.

FIGS. 1 and 2 show an apparatus 10 according to the present invention which is useful for providing radiation treatment to the tissue lining of a body cavity. Apparatus 10 includes a balloon-tube 14 having a distal end 16 and a proximal end 20, and includes an inelastic, spherical balloon 12 attached to distal end 16. Balloon-tube 14 is hollow and defines an interior channel 22 extending along and about a balloon-tube axis 30. Interior channel 22 is connected with an interior region of balloon 12 such that inflation and deflation of balloon 12 is controllable from the proximal end 20 of balloon-tube 14. FIG. 1 shows balloon 12 inflated and FIG. 2 shows balloon 12 deflated, with the balloon 12 being collapsed around an axis 13 extending coaxially from axis 30.

When inflated, balloon 12 defines a balloon diameter 13, a proximal end of which is located at the center of the distal end 16 of the balloon-tube 14 and a distal end of which is at the oppoite side of the balloon. Balloon diameter 13 will be referred to herein below as the balloon-attachment axis, or more simply as the balloon-axis. Generally, immediately after inflation, the diameter (or balloon axis) 13 is not aligned with the control axis of the balloon-tube 14.

Preferably, balloon 12 contains a reference, or fiducial, region or mark 18 at the distal end of balloon axis 13. The mark 18 is observable from the interior of the inflated balloon for facilitating alignment of balloon-tube axis 30 and the inflated balloon axis 13, as will be discussed further below. Thus, reference mark 18 is preferably located where axis 13 intersects the surface of balloon 12 as shown in FIG. 1. In alternative embodiments, reference region 18 may include a plurality of marks disposed in a circularly symmetric pattern centered on the distal end of axis 13 and balloon 12. The mark 18 may be located either inside or outside balloon 12.

In use, balloon 12 contacts the tissue lining a body cavity and therefore is preferably composed of a biocompatable material. In the illustrated embodiment, balloon 12 is an inelastic balloon, meaning that inflation will expand balloon 12 to a predetermnined shape and further inflation will not further alter the balloon's shape but will only increase interior pressure, and accordingly, the rigidity of the balloon. Balloon 12 is also preferably transparent, so body surfaces and any external reference mark can be viewed from the interior of the inflated balloon.

The balloon-tube 14 is sized to permit insertion into a cannula which in turn is sized to facilitate insertion into body passageways such as the urethra, and the balloon is preferably chosen so that when deflated, as shown in FIG. 2, the balloon 12 can be packed into a region having a diameter no larger than that of the inner diameter of the cannula, or more preferably no larger than the outer diameter of the balloon-tube 14.

The apparatus of the present invention may also include an electron-beam (e-beam) activated x-ray source. That source may operate at relative low energy as in the range of approximately 10 kV to 90 kV, and relatively small electron beam currents, as in the range of approximately 1 nA to 1 mA. Such a source is described more completely in the above-referenced U.S. Pat. No. 5,153,900 granted to Nomikos et al.

Figure 3:
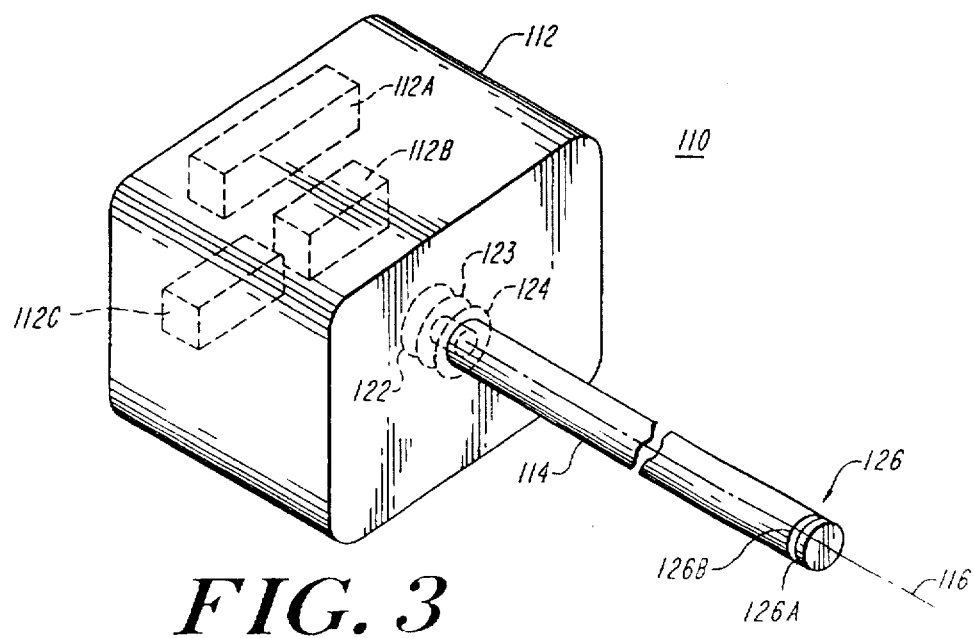
FIG. 3 is a perspective view of a miniature x-ray probe according to the invention.

FIG. 3 shows such an x-ray source 110 which includes an elongated cylindrical probe 114 extending along a reference axis 116 from a housing 112 and having a target assembly 126 at its distal end. The housing 112 encloses a power supply 112A. The probe 114 is a hollow tube having at its proximal end an electron beam generator (cathode) 122 and an associated high voltage power supply 112A. Cathode 122 is located in close proximity to an annular focusing electrode 123 typically at nearly the same potential as the cathode 122. The hollow, tubular probe 114, the cathode, grid, and the hole in the anode all extend along an axis 116. An associated controller controls the greater of these elements to generate an e-beam, and direct that beam along axis 116 to the target assembly 126. The target assembly, in response to this incident e-beam, generates x-rays. In various embodiments, parts of the probe 114 are preferably selectively shielded to control the spatial distribution of x-rays. In addition, the probe 114 is preferably magnetically shielded to prevent external magnetic fields from deflecting the beam away from the target.

Figure 4:
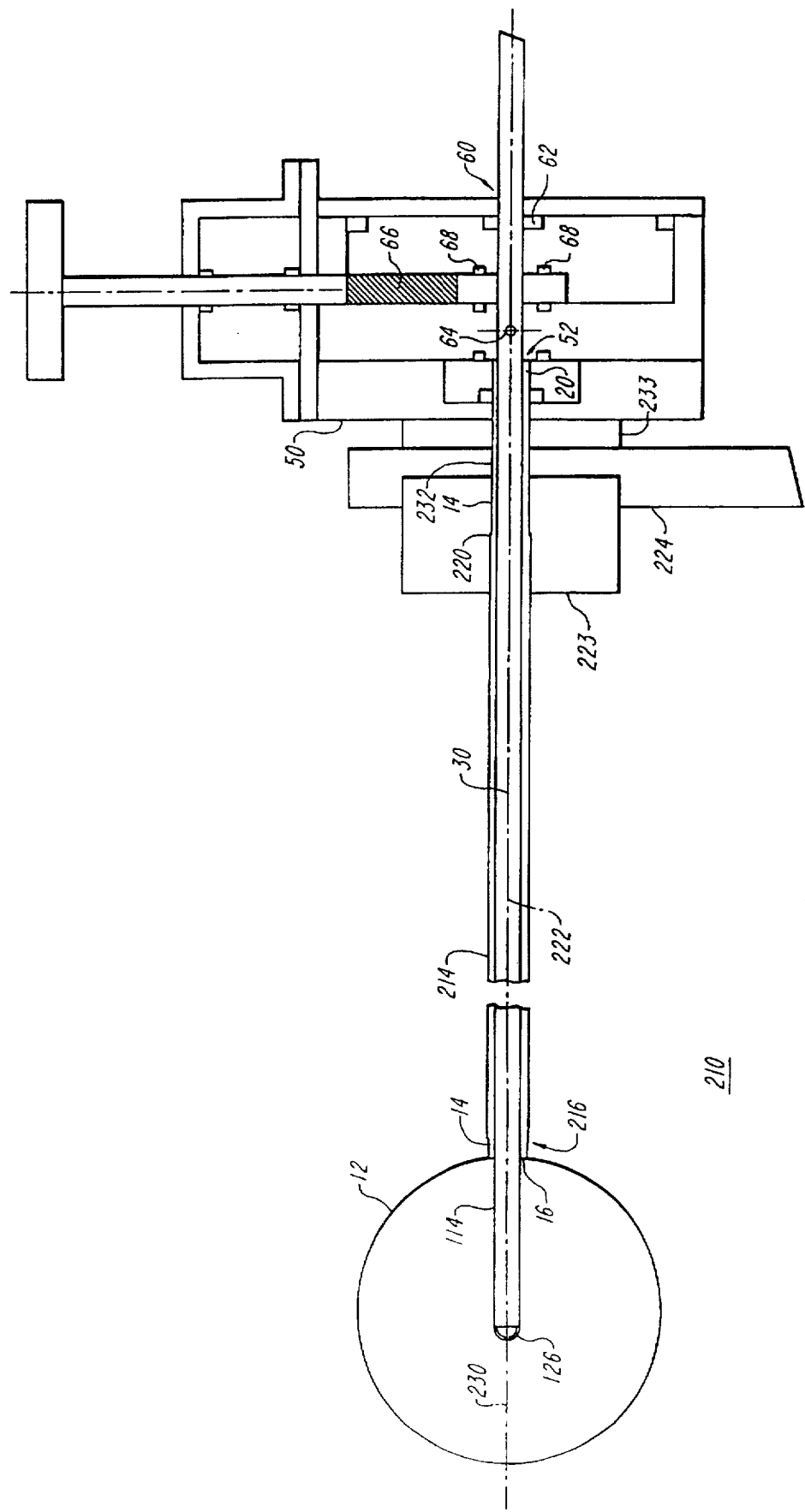
FIG. 4 is a cross sectional view of a kit according to the invention containing a miniature x-ray probe, a balloon-tube, a balloon, and a guidance cannula.

FIG. 4 shows a kit 210 according to the invention for delivering x-rays to the tissue lining a body cavity. Kit 210 includes balloon 12, balloon-tube 14, and x-ray probe 114 (housing 112 is not shown). Kit 210 further includes an elongated tubular cannula 214. Cannula 214 defines an axis 230 and has an inner diameter slightly larger than the outer diameter of balloon-tube 14, such that balloon-tube 14 and balloon 12 when deflated are slidably positionable within an interior channel 222 of cannula 214 so that balloon-tube axis 30 is substantially coaxial with cannula axis 230. Preferably, the walls of cannula 214 includes interior channels which permit flow therethrough of a fluid coolant. Preferably, the walls of cannula 214 also include channels permitting flow of urine from the bladder, as well as the flow of gas into the bladder (so that the bladder can be inflated to facilitate inflation of the balloon 12).

A proximal end 220 of cannula 214 is integrally mounted to a cooled-cannula water and urine manifold 223 which is supported by a docking clamp (or block) 224 useful for aligning cannula 214 as will be discussed further below. Manifold 223 also allows gas (preferably ($CO_2$) to be introduced through the urine channel in order to inflate the bladder. Balloon inflation is accomplished by means of gas inlet 64 as described below.

In a preferred embodiment the cannula 214 is constructed from surgical steel or other biocompatable material. In use, the cannula 214 is inserted into body passageways, such as the urethra, or surgically made passageways. Since cannula 214 is relatively rigid, balloon-tube 14 may be relatively flexible and may be fabricated from, for example, light weight, thin, plastic.

FIG. 4 shows proximal end 20 of balloon-tube 14 integrally mounted in a pressure-lock module 50, which provides for the introduction of gas pressure into the balloon and subsequent introduction of an endoscope or the x-ray probe into the balloon without losing pressure in the balloon. Pressure-lock module 50 defines an interior channel 52 extending from proximal end 20 of balloon-tube 14 to an end 60 of pressure-lock module 50 such that interior channel 52 is connected to and coaxial with interior channel 22 of balloon-tube 14 (shown in FIG. 1). Interior channel 52 is sized such that x-ray probe 114 is slidably positionable within channel 52.

The balloon-tube 14 is affixed to pressure-lock module 50 by way of a clamp 233. FIG. 4 shows balloon-tube 14 inserted within cannula 214 such that the distal end 16 of balloon-tube 14 extends beyond a distal end 216 of cannula 214. In this position, balloon 12 is free to expand without being constricted by cannula 214. FIG. 4 further shows x-ray probe 114 inserted within balloon-tube 14 such that x-ray target 126 is centered within inflated spherical balloon 12.

Pressure-lock module 50 includes a sealing O-ring 62 for forming an air-tight seal with probe 114 for preventing pressurized gas from escaping inflated balloon 12 when probe 114 is inserted within channel 52. O-ring 62 is preferably made of rubber or other resilient material suitable for forming air-tight seals. In addition to O-ring 62, pressure-lock module 50 may include other O-rings distributed in a conventional fashion through module 50 to assist in forming a gas-tight seal with probe 114.

Pressure-lock module 50 further provides a pressure port 64 which may be coupled to a tank of pressurized gas or a pump (not shown) for controlling inflation and deflation of balloon 12. Pressure-lock module 50 further provides gate valve 66 and O-rings 68 for sealing channel 52 and thereby maintaining pressure within balloon 12 when the x-ray probe or an endoscope are not present in O-ring 62. Gate valve 66, which is shown in an open position in FIG. 4, is slidably mounted within pressure-lock module 50. In its open position, gate valve 66 does not obstruct channel 52 and allows probe 114 to be inserted into balloon-tube 14. When probe 114 is withdrawn, gate valve 66 can slide downwards such that O-rings 68 and gate valve 66 form a gas-tight seal preventing gas from flowing between the interior of balloon 12 and end 60 of pressure-lock module 50.

Pressure lock module 50 thus provides several methods for controlling the inflation and deflation of balloon 12 while introducing either the probe or endoscope into the balloon. For example, if balloon 12 is initially deflated, gate valve 66 may be moved downwards to its closed position and a gas pump (not shown) can pump gas through pressure port 64 into balloon 12 until the balloon is inflated to a desired pressure. Gate valve 66 and O-rings 68 prevent any gas from escaping through end 60. Once probe 114, or other such instrument, is inserted into channel 52 such that target end 126 is beyond O-ring 62, gate valve 66 can be retracted to its open position as shown in FIG. 4. The seal formed by O-ring 62 and probe 114 will prevent any gas from escaping the balloon. Probe 114 can then be inserted such that target 126 is positioned at a desired location within inflated balloon 12 as shown in FIG. 4. This final insertion of probe 114 increases the pressure inside balloon 12 slightly because probe 114 drives some of the gas that was inside channel 22 into balloon 12. This slight increase in pressure is generally negligible and does not interfere with the operation of kit 210. However in some situations, it is desirable to connect a pressure control valve (not shown) to port 64 to maintain constant pressure within balloon 12 as probe 114 is being inserted.

The operation of kit 210 will now be discussed in connection with providing an exemplary radiation treatment to a bladder. As those skilled in the art will appreciate, radiation treatment of other body cavities can be accomplished in a similar manner. Referring to FIGS. 5A and 5B, initially cannula 214 is inserted into the urethra of a patient such that distal end 216 is positioned near the intersection of a urethra and a bladder 300. Proximal end 220 of cannula 214 remains outside the body of the patient. The body wall of the patient is shown schematically at 302 in FIG. 5A. As is further shown in FIG. 5A, the bladder 300 initially has an irregular shape.

In the preferred embodiment, kit 210 includes a V-guide 410 used for alignment as will be discussed further below. V-guide 410 provides a surface bearing a V-shaped groove 412 extending along an axis 430. Docking clamp 224 may be fixed to one end of V-guide 410, and manifold 223 may be clamped to docking clamp 224. When manifold 223 is clamped to docking clamp 224, the cannula axis 230 of cannula 214 is parallel to axis 430 of V-guide 410.

Once cannula 214 is inserted into the patient so that the distal end 216 is positioned near the intersection of the urethra and the bladder, V-guide 410 and cannula 214 are aligned by clamping manifold 223 to docking clamp 224. Next, pressure-lock module 50 is positioned on V-shaped groove 412 as shown in FIG. 5A. When pressure-lock module 50 is positioned on groove 412, the balloon-tube axis 30 of balloon-tube 14 is substantially coaxial with cannula axis 230. Initially, balloon 12 is deflated and is packed so that it extends along central axis 30 and so that the outer diameter of balloon 12 does not exceed the outer diameter of balloon-tube 14. Pressure-lock module 50 is then advanced along groove 412 towards docking clamp 224 so that deflated balloon 12 and balloon-tube 14 are inserted through cannula 214. Preferably, the components are sized so that when pressure-lock module 50 abuts docking clamp 224, the distal end 16 of balloon-tube 14 extends just beyond the distal end 216 of cannula 214 so that balloon 12 extends into the bladder 300.

Figure 6:
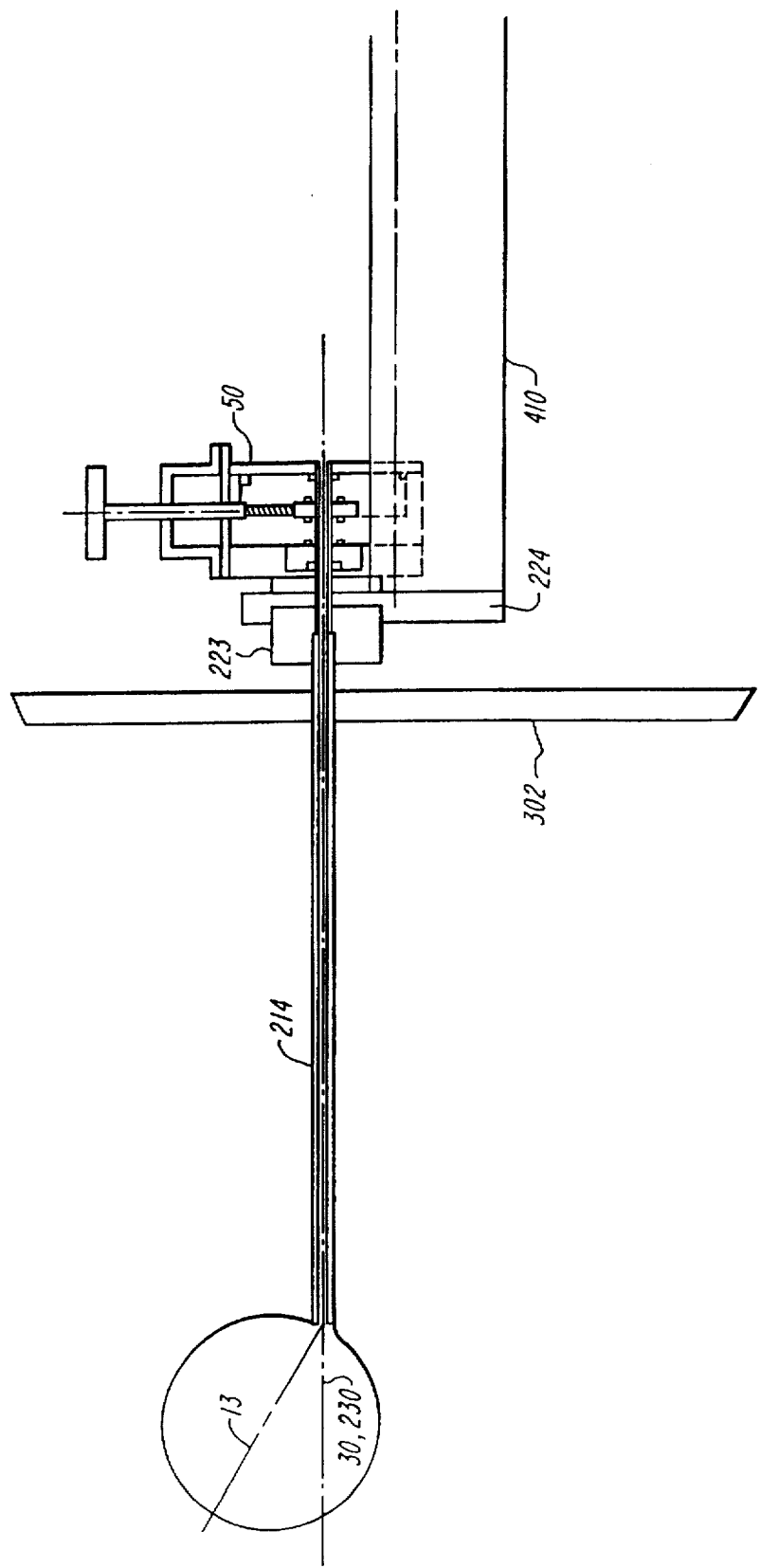
FIG. 6 is a side view of the kit shown in FIGS. 5A and 5B, showing the balloon-tube inserted within the cannula.

FIG. 6 shows pressure-lock module 50 abutting docking clamp 224 and balloon 12 inflated so that balloon 12 has stretched bladder 300 to a uniform spherical shape. In many cases it is desirable to inflate bladder 300 (via gas flow in the urine channels of cannula 214) prior to inflation of balloon 12 so that minimal stress is applied to the bladder during inflation of the balloon. As is shown in FIG. 6, after balloon 12 is inflated, internal pressures from the patient's body typically cause balloon 12 to shift relative to cannula 214 so that balloon axis 13 is angularly offset with respect to cannula/balloon-tube axes 30, 230. This misalignment occurs because, even though balloon 12 is inelastic or non-stretchable, the junction between balloon 12 and guidance tube 14 is flexible. As a consequence of such a misalignment of axes 13 and 30, it is difficult to insert an x-ray probe 114 through guidance tube 14 so that its tip 126 is positioned at the center of balloon 12.

Figure 7:
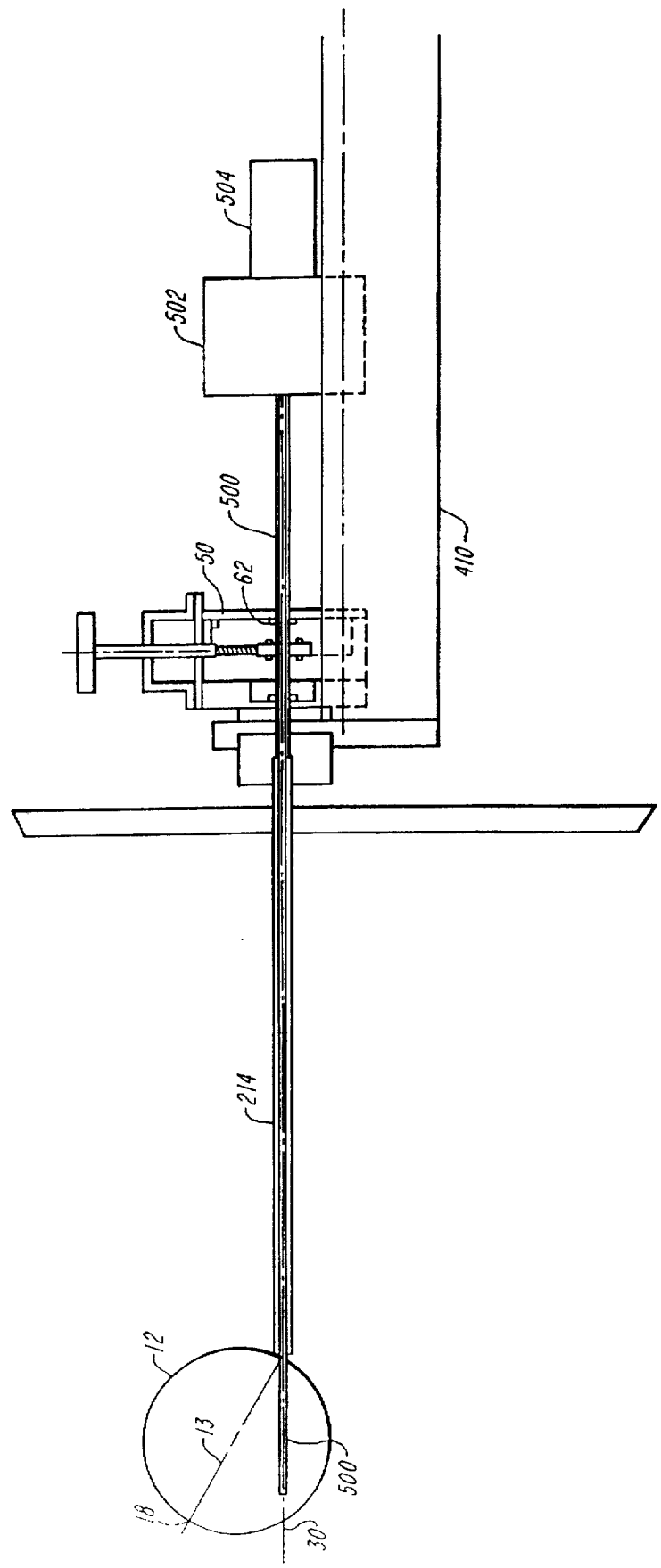
FIG. 7 shows an apparatus according to the invention in which the balloon is inflated within a body cavity and an endoscope has been inserted through the balloon-tube and into the balloon.

FIG. 7 shows an endoscope 500 inserted into the balloon 12. The misalignment of axes 13 and 30 can be corrected by rotating V-guide 410 concurrently with cannula 214 and balloon-tube 14 about distal end 16 of the balloon-tube (which has been previously located near the neck of the bladder, i.e., the intersection of the urethra and the bladder, which is the most anatomically desirable point of rotation for the tubes). The alignment of axes 13 and 30 can be confirmed by use of an endoscope, or other optical viewing instrument, for viewing fiducial mark 18.

As is well known in the art, endoscopes are normally constructed from optical fibers or lenses held in alignment by an elongated cylindrical casing. The outer diameter of endoscope 500 is preferably chosen to be similar to that of X-ray probe 114 so that endoscope 500 forms a gas-tight seal with pressure-lock module 50. Insertion of endoscope 500 into balloon-tube 14 therefore does not cause loss of pressure from balloon 12. Endoscope 500 is shown fixed to a cylindrical endoscope holder 502 which is sized so that when holder 502 rests on V-groove 412 the axis of endoscope 500 is coaxial with the axis 30 of balloon-tube 14 (shown in FIG. 4) so that endoscope 500 may be inserted into balloon-tube 14 simply by advancing holder 502 along V-groove 412 towards pressure lock module 50. A CCD camera 504 is attached to holder 502 to provide a display of the interior of balloon 12 as viewed by endoscope 500. The optics of endoscope 500 preferably contain cross-hairs which are aligned with the central axis of the endoscope 500. Alignment of balloon axis 13 and balloon-tube axis 30 may be achieved by aligning the cross-hairs of endoscope 500 with fiducial mark 18.

Once alignment of axes 13 and 30 has been achieved, V-guide 410 is preferably locked into the proper position to preserve the alignment. Kit 210 preferably includes a multi-axis support system for supporting V-guide 410 (as shown in FIGS. 8A-B). FIGS. 8A and 8B show front and side views, respectively, of a multi-axis support system 600. Preferably, support system 600 provides at least five degrees of freedom (x, y, z, θ (polar angle) and Φ (azimuth angle)) so that it can conveniently support V-guide 410 at any arbitrary angle while keeping the distal end of the balloon-tube fixed in space. FIG. 8A shows pressure-lock module 50 and endoscope holder 502 resting on V-guide 410, and support system 600 supporting V-guide 410. V-guide 410 is positioned so that axes 13 and 30 are not aligned. Once alignment has been achieved, the positions of V-guide 410 and support system 600 are preferably fixed, or locked, so that a surgeon may remove endoscope 500 and subsequently insert x-ray probe 114 without fear of disturbing the alignment.

Withdrawal of endoscope 500 and insertion of probe 114 are accomplished without loss of pressure from balloon 12 by use of gate valve 66 (since loss of pressure from, and reinflation of, balloon 12 may disturb the alignment). Withdrawal of endoscope 500 is accomplished by retracting holder 502 so that the distal tip of endoscope 500 is retracted just beyond gate valve 66 and such that it is still forward of O-ring 62 so that endoscope 500 still maintains a gas-tight seal with pressure-lock module 50. Gate valve 66 is then moved to its closed position (as shown in FIG. 6) and endoscope 500 is completely withdrawn from pressure-lock module 50. Probe 114 is then inserted into pressure-lock module 50 so that target 126 is forward of O-ring 68 so that probe 114 forms a gas-tight seal with pressure-lock module 50. Gate valve 66 is then moved to its open position and probe 114 is inserted into balloon 12.

Figure 9:
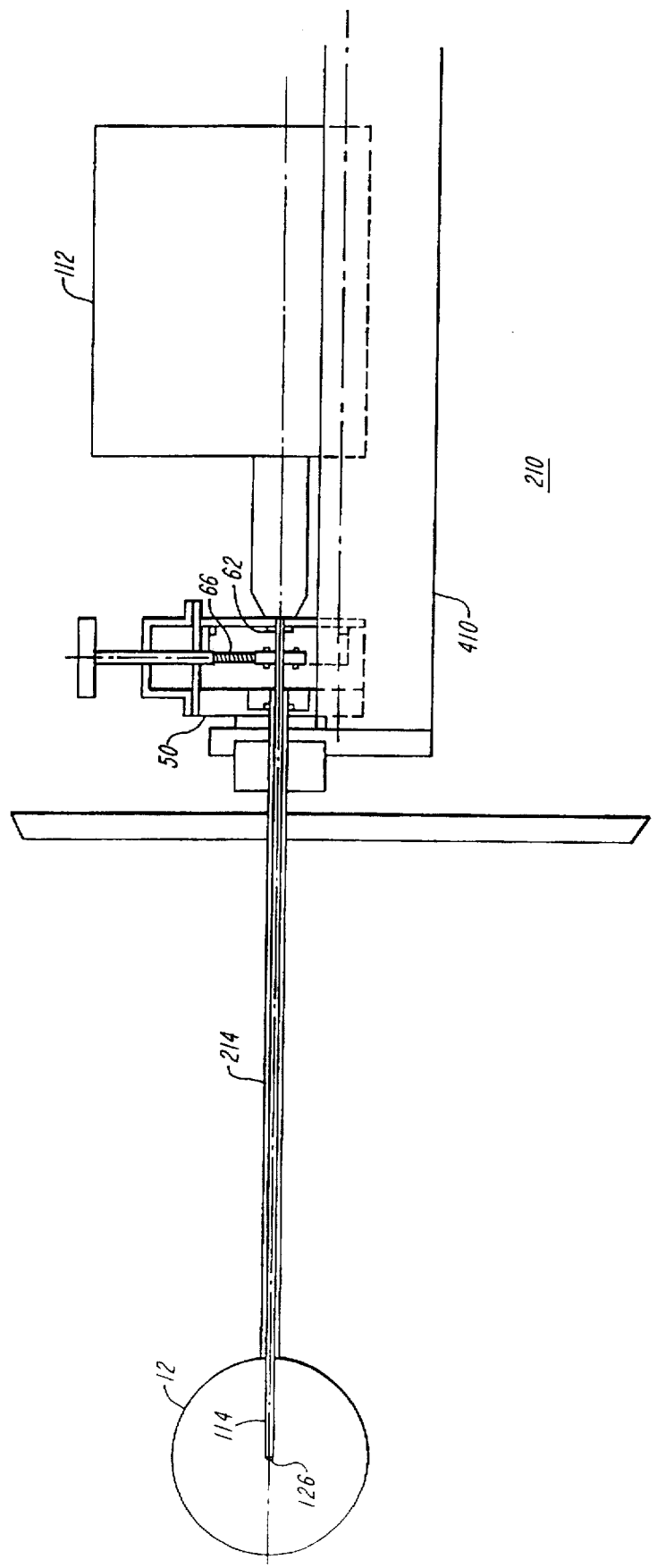
FIG. 9 shows the apparatus of FIG. 8 in which the balloon attachment axis and the balloon-tube axis have been aligned with each other via use of an endoscope and subsequently an x-ray probe has been inserted within the balloon.

FIG. 9 shows probe 114 inserted so that target 126 is centered within inflated balloon 12. Housing 112 of probe 114 is configured so that when housing 112 rests on V-groove 412, probe 114 is aligned with axis 30 of balloon-tube 14 so that probe 114 may be inserted into balloon-tube 14 simply by advancing housing 112 along V-groove 412 towards pressure-lock module 50. Further, housing 112 and probe 114 are preferably sized so that when housing 112 abuts pressure-lock module 50, target 126 is centered within inflated balloon 12.

Once target 126 is centered within balloon 12, x-ray source 110 is operated to direct an e-beam to be inadent on target 126, which in turn generates x-rays. Since target 126 acts as a nominal point source, it generates an x-ray field having spherical isodose contours. Therefore, a uniform dose of x-rays is delivered to the tissue lining the bladder 300.

After treatment, probe 114 is removed, and then balloon 12 is deflated as described above. Deflated balloon 12, guidance tube 14 and cannula 214 are then withdrawn from the body.

Accordingly, kit 210 allows delivery of a uniform dose of x-rays to the tissue lining a body cavity. Since the x-rays are generated from within the cavity, the x-rays need not first penetrate the patient's bone mass or skin, and other tissue prior to reaching the target site. Thus, kit 210 allows delivery of a uniform dose of x-rays to the target tissue substantially without radiating non-targeted tissue. Further, since the x-rays need not first penetrate non-target tissue prior to reaching the target site, relatively low energy x-rays can be used, compared to the prior art.

Figure 10:
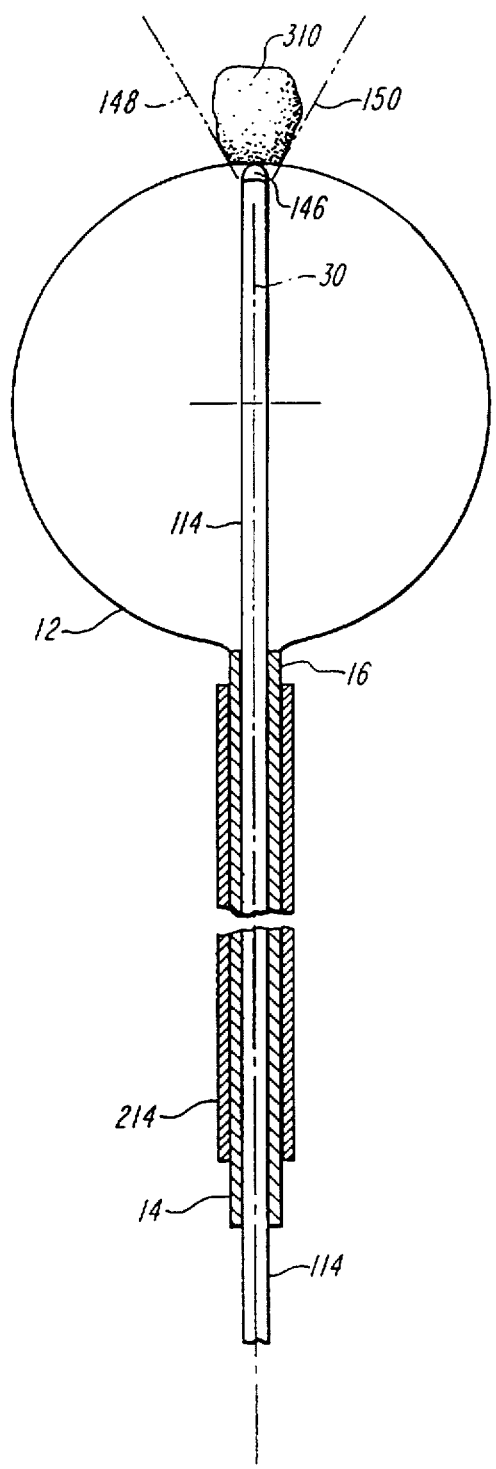
FIG. 10 shows an apparatus according to the invention useful for treating localized tumors in the bladder.

In addition to providing a uniform dose of radiation to tissue lining a body cavity as has been described above, apparatus according to the invention may also be used to provide a specifically contoured dose useful for treating a tumor or other local lesion. FIG. 10 shows an apparatus for treating a tumor 310. In this embodiment, the normal probe tip of x-ray probe 114 which generally acts as a point, or omnidirectional, source of x-rays is replaced with a probe tip 146 which generates an x-ray field having a specific controlled spatial distribution. Probe tip 146 is generally fabricated by covering the normal probe tip with a variable thickness x-ray shield, or a shadow mask as it is sometimes called in the art. The structure of such x-ray shields is more fully discussed in the above-referenced U.S. patent application Ser. No. 08/184,271, entitled X-ray Source with Shaped Radiation Pattern.

Probe tip 146 is preferably positioned so that it almost touches balloon 12 adjacent to tumor 310, and probe 114 is then operated to generate x-rays. As shown in FIG. 10, probe tip 146 generates an x-ray field contained within the boundaries shown by lines 148 and 150, so tumor 310 is effectively radiated while only a minimal amount of healthy tissue is exposed to radiation.

The above-described methods of aligning tube 14 and balloon 12 are also useful in treating tumor 310. For example, after inflation of balloon 12, an endoscope may be inserted to locate tumor 310. Once alignment has been achieved between axis 30 of balloon-tube 14 and tumor 310, the endoscope is withdrawn and probe 114 is inserted until target 146 almost makes contact with the interior surface of balloon 12.

Figure 11:
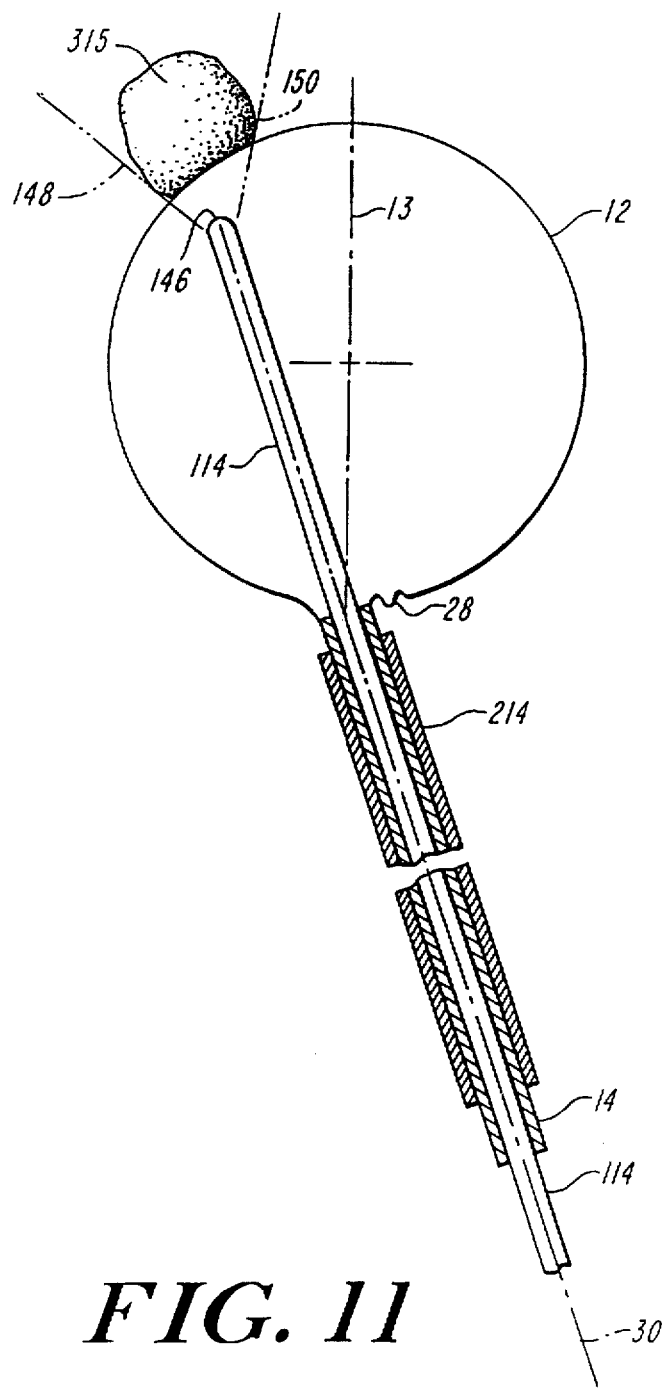
FIG. 11 shows the apparatus shown in FIG. 10 being used to treat a localized tumor that is not directly opposite the distal end of the guidance tube.
Figure 12:
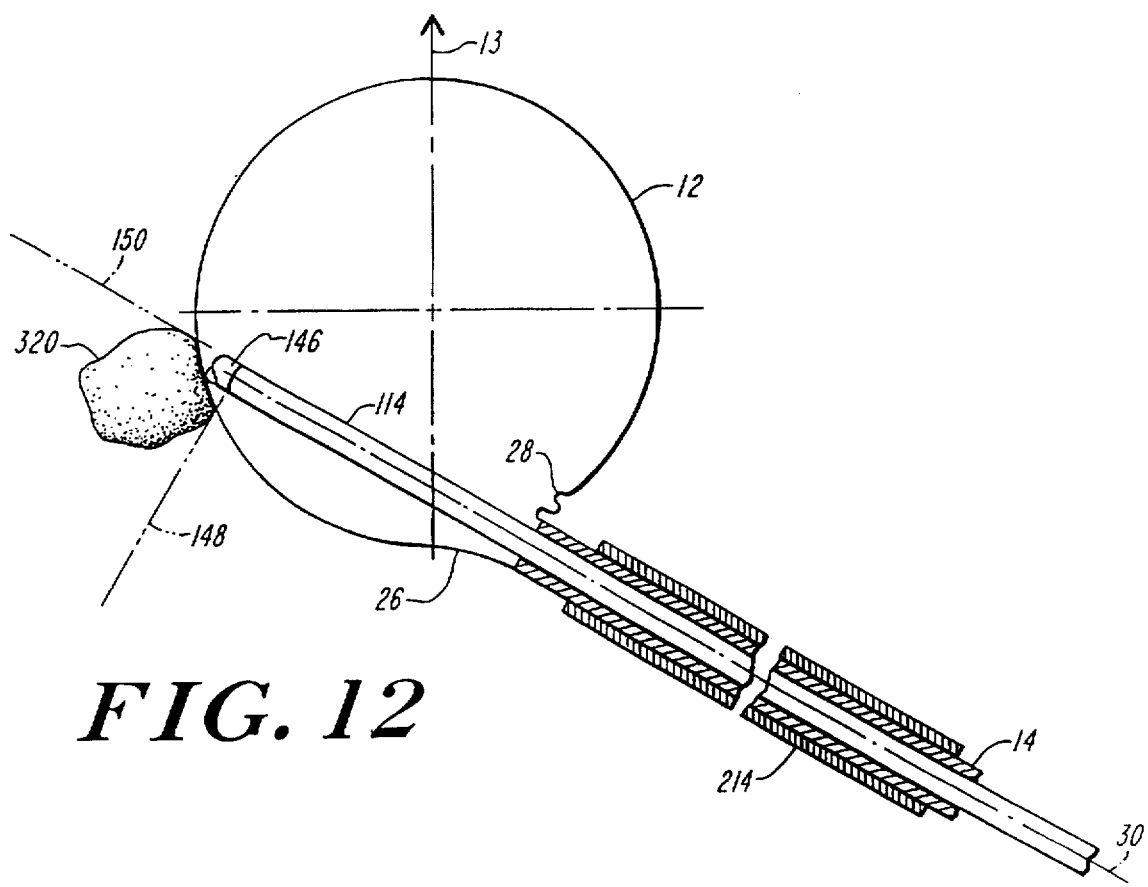
FIG. 12 shows the apparatus shown in FIG. 10 being used to treat a localized tumor that is relatively close to the intersection of the urethra and the bladder.
Figure 13:
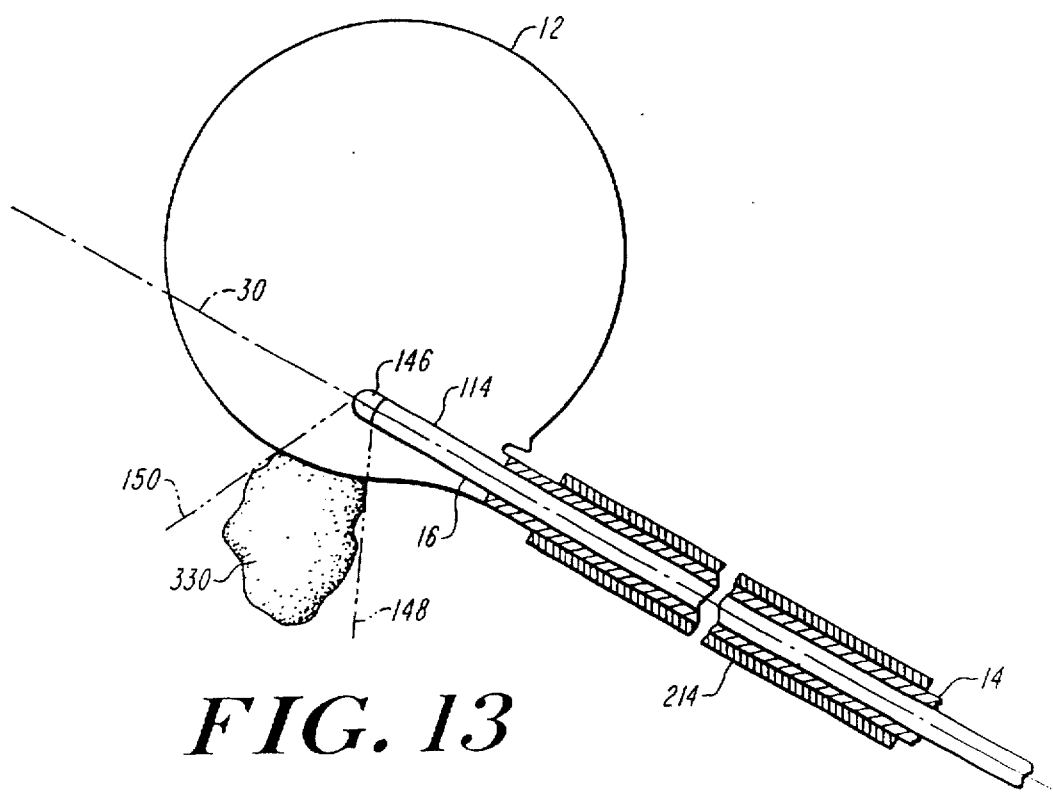
FIG. 13 shows the apparatus shown in FIG. 10 being used to treat a localized tumor that is even closer to the intersection of the urethra and the bladder than the tumor shown in FIG. 12.

FIG. 10 shows treatment of a tumor 310 that is directly opposite the distal end 16 of balloon-tube 14. As shown in FIGS. 11-13, the same apparatus is useful for treating tumors which are located in different regions of the bladder. The tumor 315 shown in FIG. 11 is also on the dome of the bladder but displaced from the apex. Therefore, to position probe tip 146 adjacent tumor 315, tube 14 is aligned such that balloon-tube axis 30 is not coaxial with balloon axis 13.

Alignment may be accomplished as described above by using an endoscope to align balloon-tube axis 30 with tumor 315. Axes 13 and 30 can be misaligned either because they were misaligned due to manufacturing imperfection, the balloon has been pushed to one side by body forces or the cannula has been purposely misaligned in order to place the probe near a tumor on the wall of the body cavity. In the latter two cases crinkle 28 develops in balloon 12 as shown in FIG. 11. Since the balloon material is essentially inelastic there will be no stretching of the balloon to accommodate the misalignment of axes 13 and 30. After alignment, x-ray probe 114 is inserted into tube 14 until target 146 almost contacts the surface of balloon 12 adjacent to tumor 315. Again probe tip 146 is appropriately masked such that x-rays emitted from target 146 are confined within boundaries indicated by lines 148 and 150.

FIG. 12 illustrates treatment of a tumor 320 that is even closer to the junction of the urethra and the bladder than is tumor 315 shown in FIG. 11. Treatment of tumor 320 is accomplished by aligning axis 30 of guidance tube 12 with tumor 320 as described above. In the preferred embodiment, the connection between balloon 12 and tube 14 will permit alignments such that the angle between balloon axis 13 and guidance tube axis 30 is adjustable between zero and 90 degrees. After alignment, x-ray probe 114 is inserted into tube 14 until probe tip 146 almost contacts the surface of balloon 12 adjacent to tumor 320. Again probe tip 146 is appropriately masked such that x-rays emitted from target 146 are confined within boundaries indicated by lines 148 and 150.

FIG. 13 shows treatment of a tumor 330 that is even closer to the intersection of the urethra and the bladder than is tumor 320 shown in FIG. 12. Tumor 330 is so close to the intersection of the urethra and the bladder that it is not possible to align axis 30 with tumor 330. In this case treatment is accomplished by placing probe tip 146 as close as possible to tumor 330. One method of positioning the probe tip at the optimal treatment location is to use the endoscope to locate the tumor and measure the distance that the endoscope has been inserted into the balloon when the tip of the endoscope is as close as possible to the tumor. Then the x-ray probe tip can subsequently be placed at the same position since the probe is of known length. Again, probe tip 146 is selected such that x-rays generated therefrom are confined within boundaries indicated by lines 148 and 150 and tumor 330 is radiated while exposing only a minimal amount of healthy tissue to x-rays. As those skilled in the art will appreciate, the treatment time of tumor 330 will be longer to compensate for the distance between target 146 and tumor 330 due to the $1/R^2$ decrease in radiation intensity with distance. Alternatively, the treatment time may remain constant if the power delivered by the x-ray probe is correspondingly increased.

The invention may be embodied in other specific forms without departing from the spirit or essential characteristics thereof. For example, the invention has been described in terms of use with a spherical balloon for treatment of the bladder. As those skilled in the art will appreciate, balloons with other shapes are useful for treatment of other body cavities, e.g., a cylindrical balloon may be useful in conjunction with treatment of the colon.

The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A balloon-tube assembly for stretching a body cavity to a predetermined shape, comprising:
   A. a tube extending along a central axis and having a proximal end and a distal end, said tube defining an interior channel extending along said central axis,
   B. an inflatable substantially inelastic balloon affixed to and extending from said tube at points near said distal end of said tube, said balloon when inflated defining a predetermined surface contour disposed about an interior region extending along a balloon axis, said interior channel and interior region of said balloon being contiguous, and said balloon axis intersecting said central axis near said distal end of said tube, and
   C. alignment means operative from said proximal end of said tube, for selectively aligning said balloon axis and said central axis to a predetermined angular orientation.

2. An assembly according to claim 1, wherein said angular orientation is adjustable between zero degrees and at least 90 degrees.

3. An assembly according to claim 1, wherein said alignment means comprises a reference region on said balloon, the position of said reference region relative to said central axis being determinable from within said interior region.

4. An assembly according to claim 3, wherein said reference region is in the interior region of said balloon and wherein said reference region fluoresces in response to incident light in a predetermined spectral range.

5. An assembly according to claim 4, further including means for irradiating said reference region with light in said predetermined spectral range and including means for detecting fluorescent light generated by said reference region.

6. An assembly according to claim 1, further including inflation means for controlling a pressure in said balloon interior region, said inflation means disposed near said proximal end.

7. An assembly according to claim 6, wherein said inflation means includes a gas flow path extending between said interior channel and a pressure source.

8. An assembly according to claim 1, wherein said balloon when inflated is symmetrically disposed about said balloon axis.

9. An assembly according to claim 1, wherein said predetermined surface contour is spherical.

10. An assembly according to claim 1, wherein said predetermined surface contour is cylindrical.

11. An assembly according to claim 1, wherein said tube includes an interior wall and an exterior wall wherein said interior wall defines one boundary of said interior channel, wherein said guidance tube includes a cooling channel between said interior wall and said exterior wall extending from a fluid inlet in said exterior wall to a fluid outlet in said exterior wall.

12. An assembly according to claim 11, wherein said fluid inlet and said fluid outlet are near said proximal end.

13. An assembly according to claim 12, wherein said cooling channel extends to a point near said distal end.

14. An assembly according to claim 1, said balloon when deflated being collapsible into a volume extending along an axis substantially parallel to said central axis.

15. An assembly according to claim 1, wherein said tube is characterized by an outer diameter, said balloon when deflated being collapsible into a volume having an outer diameter less than or equal to said outer diameter of said tube.

16. A kit for applying x-rays to an interior surface of a body cavity, said kit comprising:

A. an x-ray source guidance assembly, said assembly including:
   i. a guidance cannula extending along a cannula axis end having a proximal end and a distal end, said guidance cannula defining an interior channel extending along said cannula axis,
   ii. a balloon-tube extending along a central axis and having a proximal end and a distal end, said balloon-tube defining an interior channel extending along said central axis, said balloon-tube being insertable within said interior channel of said guidance cannula, and
   iii. an inflatable substantially inelastic balloon affixed to and extending from said tube at points near said distal end of said balloon-tube, said balloon when inflated defining a predetermined surface contour disposed about an interior region extending along a balloon axis, said interior channel of said balloon-tube and said interior region of said balloon being contiguous, and said balloon axis intersecting said central axis near said distal end of said tube, B. an x-ray source cooperative with said tube, said x-ray source including an x-ray generator disposed at or near a target end of an elongated tubular element wherein said tubular element is slidably positionable within said interior channel such that said target end is positionable within said balloon when inflated.

17. A kit according to claim 16, further comprising alignment means for selectively aligning said balloon axis and said central axis to a predetermined angular orientation.

18. A kit according to claim 17, wherein said angular orientation is adjustable between zero degrees and at least 90 degrees.

19. A kit according to claim 17 wherein said alignment means comprises a reference region on said balloon, the position of said reference region relative to said central axis being determinable from within said interior region.

20. A kit according to claim 19, wherein said reference region is in the interior region of said balloon and wherein said reference region fluoresces in response to light in a predetermined spectral range.

21. A kit according to claim 20, further including means for irradiating said reference region with light in said predetermined spectral range, and including means for detecting fluorescent light generated by said reference region.

22. A kit according to claim 16, further including inflation means for controlling a pressure said balloon interior region, said inflation means disposed proximal to said tube proximal end.

23. A kit according to claim 22, wherein said inflation means includes a gas flow path extending between said interior channel and a pressure source.

24. A kit according to claim 22, wherein said inflation means provides a first channel extending along an axis substantially coaxial with said balloon-tube central axis wherein an end of said first channel is adjacent to said balloon-tube proximal end and said tubular element is slidably positionable within said first channel.

25. A kit according to claim 24, wherein said inflation means includes sealing means for maintaining the pressure in said balloon interior region when said tubular element is inserted in said first channel.

26. A kit according to claim 25, wherein said sealing means comprises an O-ring.

27. A kit according to claim 24, wherein said inflation means includes valve means for sealing said first channel thereby maintaining the pressure said balloon interior region.

28. A kit according to claim 16, wherein said balloon when inflated is symmetrically disposed about said balloon axis.

29. A kit according to claim 28, wherein said target end is positionable at a center of said balloon.

30. A kit according to claim 16, wherein said predetermined surface contour is spherical.

31. A kit according to claim 16, wherein said predetermined surface contour is cylindrical.

32. A kit according to claim 16, wherein said balloon-tube includes an exterior wall and an interior wall that defines one boundary of said interior channel, wherein said tube includes a cooling channel between said interior wall and said exterior wall extending from a fluid inlet in said exterior wall to a fluid outlet in said exterior wall.

33. A kit according to claim 32, wherein said fluid inlet and said fluid outlet are near said proximal end.

34. A kit according to claim 33, wherein said cooling channel extends to a point near said distal end.

35. A kit according to claim 16, wherein said x-ray generator is an omnidirectional generator.

36. A kit according to claim 16, wherein said target end includes a shield means for controlling a spatial distribution of isodose contours of said x-rays emitted by said x-ray generator.

37. A kit according to claim 36, wherein said shield means includes a shield cover characterized by a selected x-ray transmission profile, wherein said shield cover is disposed adjacent to said x-ray generator.

38. A kit according to claim 16, wherein said distal end of said cannula is positionable inside the body near the body cavity, and wherein said tube and said balloon when deflated are slidably positionable within said cannula.

39. A kit according to claim 38, further including alignment means, wherein said alignment means includes a guide extending along a guide axis and means for clamping said cannula such that said guide axis is parallel to said central axis of said cannula when said alignment means is clamped to said proximal end of said cannula.

40. A kit according to claim 39, wherein said proximal end of said cannula is slidably mountable on said guide such that said cannula is slidably positionable within said cannula when said proximal end of said cannula is mounted on said guide.

41. A kit according to claim 40, wherein a proximal end of said x-ray source is slidably mountable on said guide such that said target end is slidably positionable within said cannula when said proximal end of said x-ray source is mounted on said guide.

42. A kit according to claim 16, said balloon when deflated being collapsible into a volume extending along an axis substantially parallel to said central axis.

43. A kit according to claim 16 wherein said cannula is characterized by an inner diameter, said balloon when deflated being collapsible into a volume having an outer diameter less than or equal to said inner diameter of said cannula.

* * * * *